US006030805A

United States Patent [19]

Normark et al.

[11] Patent Number: 6,030,805

[45] Date of Patent: Feb. 29, 2000

[54] FIBRONECTIN BINDING PROTEIN AS WELL AS ITS PREPARATION

[76] Inventors: Staffan Normark, S-913 00 Holmsund, Zackrisvägen; Arne Olsen, 902 41 Umea, Sprakgränd 19, both of Sweden

[21] Appl. No.: 08/495,959

[22] Filed: Jun. 28, 1995

Related U.S. Application Data

[63] Continuation of application No. 08/318,519, Oct. 5, 1994, abandoned, which is a continuation of application No. 08/187,865, Jan. 28, 1994, abandoned, which is a continuation of application No. 07/970,846, Nov. 3, 1992, abandoned, which is a continuation-in-part of application No. 07/789,437, Nov. 6, 1991, abandoned, which is a continuation of application No. 07/347,189, May 4, 1989, abandoned.

[51] Int. Cl.$^7$ .................................................... C12P 21/00

[52] U.S. Cl. .................. 435/69.1; 435/320.1; 435/252.3; 536/23.7

[58] Field of Search ............................... 435/69.1, 252.3, 435/33, 320.1; 536/22.1, 23.1, 23.7

[56] References Cited

PUBLICATIONS

Froman et al–*J. Biol. Chem.* 259(23):14899–14900 (1984).
Glover–"Gene Cloning: The Mechanics of DNA Manipulation" pub. 1984 by Chapman and Hall (London), pp. 1–20.

*Primary Examiner*—Robert A. Wax
*Assistant Examiner*—Daniel S. Mytelka
*Attorney, Agent, or Firm*—Burns, Doane, Swecker & Mathis, L.L.P.

[57] ABSTRACT

The present invention relates to a new fibronectin binding protein from *E. coli* in the form of a curli pili. a new recombinant hybrid-DNA-molecule comprising a nucleotide sequence from *E. coli* coding for a protein or polypeptide having fibronectin binding properties. (FIG. 4).

17 Claims, 3 Drawing Sheets

```
                                                            60
AGAGACAGTCGCAAATGGCTATTCGCGTGACACAAACGTTAATTTCCATTCGACTTTTAA
                                                           120
ATCAATCCGATGGGGGTTTTACATGAAACTTTTAAAAGTAGCAGCAATTGCAGCAATCGT
                       M  K  L  L  K  V  A  A  I  A  A  I  V
                                                           180
ATTCTCCGGTAGCGCTGTGGCAGGTGTTGTTCCTCAGTACGGCGGCGGCGGTAACCACGG
  F  S  G  S  A  L  A  G  V  V  P  Q  Y  G  G  G  G  N  H  G
                                                           240
TGGTGGCGGTAATAATAGCGGCCCAAATTCTGAGCTGAACATTTACCAGTACGGTGGCGG
  G  G  G  N  N  S  G  P  N  S  E  L  N  I  Y  Q  Y  G  G  G
                                                           300
TAACTCTGCACTTGCTCTGCAAACTGATGCCCGTAACTCTGACTTGACTATTACCCAGCA
  N  S  A  L  A  L  Q  T  D  A  R  N  S  D  L  T  I  T  Q  H
                                                   ClaI    360
TGGCGGCGGTAATGGTGCAGATGTTGGTCAGGGCTCAGATGACAGCTCAATCGATCTGAC
  G  G  G  N  G  A  D  V  G  Q  G  S  D  D  S  S  I  D  L  T
                                                           420
CCAACGTGGCTTCGGTAACAGCGCTACTCTTGATCAGTGGAACGGCAAAAATTCTGAAAT
  Q  R  G  F  G  N  S  A  T  L  D  Q  W  N  G  K  N  S  E  M
                                                           480
GACGGTTAAACAGTTCGGTGGTGGCAACGGTGCTGCAGTTGACCAGACTGCATCTAACTC
  T  V  K  Q  F  G  G  G  N  G  A  A  V  D  Q  T  A  S  N  S
                                                           540
CTCCGTCAACGTGACTCAGGTTGGCTTTGGTAACAACGCGACCGCTCATCAGTACTAACA
  S  V  N  V  T  Q  V  G  F  G  N  N  A  T  A  H  Q  Y  *
                                                           600
ACGCGACCGCTCATCAGTACTAATACATCATTTCTATTACAGAAACAGGGCGCAACGTGT
                                                           660
TTTTTTTCGGGAGGAAGAATATGAATACGTTATTACTCCTTGCGGCACTTTCCAGTCAGA
         675
TAACCTTTAATAACG
```

FIG. 2

```
                                          crl
                    49kD                  60                                                        120
                                          MetThrLeuProSerGlyHisProLysSerArgLeuIleLysLysPheThrAlaLeuGlyPro
   AsnLeuLeuLysPheAlaAsnLeuValLysGlnLeuHisHisAsnArgArgLeuGln***
5'-AAATTTGCTAAAATTTGCCAATTTGGTAAAACAGTTGCATCACAACAGGAGATTGCAATGACGTTACCGAGTGGACACCCGAAGAGCAGATTGATCAAAAAATTTACCGCACTAGGCCCG

                  Lys                     180                                                        240
   TyrIleArgGluGlyLysCysGluAspAsnArgPhePhePheAspCysLeuAlaValCysValAsnValLysProAlaProGluValArgGluPheTrpGlyTrpTrpMetGluLeuGlu
5'-TATATTCGTGAAGGTAAGTGCGAAGATAATCGATTCTTTTTCGATTGTCTGGCTGTATGCGTCAACGTGAAACCGGCACCGGAAGTGCGTGAGTTCTGGGGCTGGTGGATGGAGCTTGAA
                  A      ClaI1
                                          300                                                        360
   AlaGlnGluSerArgPheThrTrySerTyrGlnPheGlyLeuPheAspLysAlaGlyAspTrpLysSerValProValLysAspThrGluValValGluArgLeuGluHisThrLeuArg
5'-GCGCAGGAATCCCGTTTTACCTACAGTTACCAGTTTGGTCTGTTCGATAAAGCAGGCGACTGGAAGAGTGTTCCGGTAAAAGACACTGAAGTGGTTGAACGACTGGAGCACACCCTACGT

                                          420                                                        480
   GluPheHisGluLysLeuArgGluLeuLeuThrThrLeuAsnLeuLysLeuGluProAlaAspAspPheArgAspGluProValLysLeuThrAla***
5'-GAGTTTCACGAGAAGCTGCGTGAACTGCTGACGACGCTGAATCTGAAGCTGGAACCGGCGGATGATTTTCGTGATGAACCGGTGAAGTTAACGGCGTGAGTGAAATGTGCCGGATGTATC
                                                                                        HpaI
                                          540                                                        600
5'-ACATCCGGCAATATCCATTAAAACTG
                 3'-AATTTTGACTATGCAGTACGG
                 ***PheGlnTyrThrMetGlyVal      phoE
```

FIG. 3

FIBRONECTIN BINDING PROTEIN AS WELL AS ITS PREPARATION

This application is a continuation of application Ser. No. 08/318,519, filed Oct. 5, 1994 now abandoned which is a continuation of application Ser. No. 08/187,865, filed Jan. 28, 1994 now abandoned which is a continuation application of U.S. Ser. No. 07/970,846, filed Nov. 3, 1992 now abandoned, which is a Continuation-In-Part (CIP) application of U.S. Ser. No. 07/789,437, filed Nov. 6, 1991 now abandoned, which is a continuation application of U.S. Ser. No. 07/347,189, filed May 4, 1989 now abandoned.

TECHNICAL FIELD

The present invention relates to a fibronectin binding protein as well as a hybrid-DNA-molecules, e.g., plasmids and phages comprising a nucleotide sequence coding for said protein. Further the invention relates to microorganims comprising said molecules and their use producing said protein, as well as the synthetic preparation of said protein.

The object of the present invention is to obtain a minimal fibronectin binding protein.

A further object of the present invention is to obtain said protein by means of a genetic engineering technique by using, e.g., a plasmid comprising a nucleotide sequence coding for said protein.

A further object is to obtain a possibility of preparing said protein by chemical synthesis.

Further objects will be apparent from the following description.

BACKGROUND OF THE INVENTION

WO-A1-85/05553 discloses bacterial cell surface proteins having fibronectin, fibrinogen, collagen and/or laminin binding ability. Thereby it is shown that different bacteria have an ability to bind to fibronectin, fibrinogen, collagen and/or laminin. It is further shown that fibronectin binding protein derived from *Staphylococcus aureus* has a molecular weight of 165 kD and/or 87 kD, whereby it is probable that the smaller protein is a part of the larger one.

Fibronectins are a family of high molecular weight glycoproteins occurring in a soluble form in many body fluids and in an insoluble form as a compound of cell surfaces, basement membranes, and extracellular matrices. Fibronectins appear to fulfil a critical role in clearance by phagocytes of autologous tissue debris, immune complexes, and bacteria. Fibronectins also bind to epithelial cells. In doing so it may serve as a receptor for organisms like group A streptococci, but may also shield the epithelial receptors of other organisms. Thus the inability of Gram negative organisms like *Ps. aeuruginosa* to colonize the oral cavity of healthy humans may be due to an interference in binding to epithelial receptors by fibronectin. The ability to resist binding to soluble fibronectin has been thought to be a virulence factor in invasive infection by group B streptococci. A number of Gram positive bacterial species including *Staphylococcus aureus*, other staphylococcus species, and group A, C and G streptococci exhibit specific interaction with fibronectin. In these species binding to fibronectin is thought to be a virulence factor enhancing colonization of wound surfaces and other fibronectin coated surfaces. *E. coli* can express a variety of adhesins with differing binding specificities. The majority of these adhesins recognize carbohydrate moieties present on glycoconjugates. *E. coli* may also express binding to matrix proteins such as fibronectin, laminin, and collagen. Uropathogenic *E. coli* expressing the 075 X adhesin bind tubular basement membranes and to the Bowman capsule known to be rich in laminin. The purified 075 X adhesin was specifically found to bind laminin. *E. coli* isolated from patients with ulcerous colitis frequently bind matrix proteins Likewise, *E. coli* isolates from bovine mastitis have been shown to bind to fibronectin at a high frequency. Below a native fibronectin binding protein from *E. coli* is disclosed, as well as the cloning of the fibronectin binding, fnbA gene from a bovine isolate of *E. coli* that express curli pili and fibronectin binding when present in *E. coli* HB101.

Chemically fibronectin is a large glycoprotein ($M_r$ about 450 kD) with two similar subunits, which may vary in molecular size depending on a complex splicing pattern of a precursor mRNA. The major function of fibronectin which is found in body fluids blood clots and extracellular matrices seems to be related to the ability of the protein to mediate substrate adhesion of most eukaryotic cells.

Figure 1:
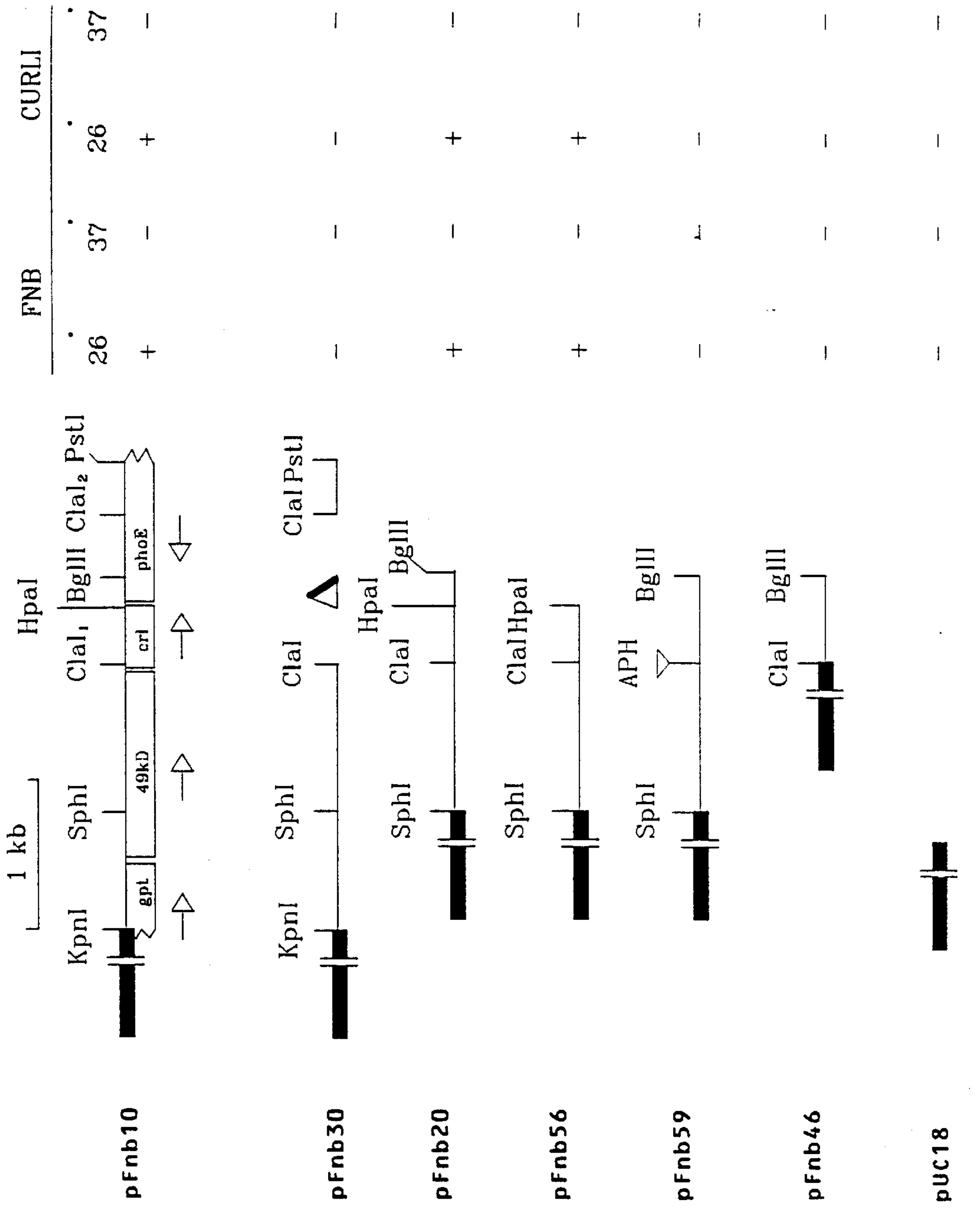
FIG. 1: Restriction map of different pFnb plasmid constructs. Fnb+ or − indicates fibronectin binding phenotype.

pFnb10 $SphI_1$-KpnI fragment in pUC18 pFnb30 ClaI cut back of pFnb10 pFnb20 BglII-SphI fragment in pUC18 pFnb56 SphI-HpaI pFnb59 APH ligated to the $ClaI_2$ site in pFnb56 pFnb46 ClaI-BglII fragment in pUC18.

FIG. 2: Restriction map and gene organization of fnb gene. The hatched boxes indicate the 17 kD.

FIG. 3: Nucleotide and predicted amino acid sequence of fnbA gene. Three stars indicate the stop codons.

DESCRIPTION OF THE PRESENT INVENTION

It has now surprisingly been found possible to obtain a native fibronectin binding protein from *E. coli*, as well as a hybrid-DNA-molecule comprising a nucleotide sequence coding for a protein or a polypeptide having fibronectin binding properties. As evident from below the following nucleotide sequence is present in the gene coding for said protein;

```
GGTGTTGTTC CTCAGTACGG CGGCGGCGGT AACCACGGTG
GTGGCGGTAA TAATAGCGGC CCAAATTCTG AGCTGAACAT
TTACCAGTAC GGTGGCGGTA ACTCTGCACT TGCTCTGCAA
ACTGATGCCC GTAACTCTGA CTTGACTATT ACCCAGCATG
GCGGCGGTAA TGGTGCAGAT GTTGGTCAGG GCTCAGATGA
CAGCTCAATC GATCTGACCC AACGTGGCTT CGGTAACAGC
GCTACTCTTG ATCAGTGGAA CGGCAAAAAT TCTGAAATGA
CGGTTAAACA GTTCGGTGGT GGCAACGGTG CTGCAGTTGA
CCAGACTGCA TCTAACTCCT CCGTCAACGT GACTCAGGTT
GGCTTTGGTA ACAACGCGAC CGCTCATCAG TACTAA.
```

corresponding to the following amino acid as identified from the N-terminal end

GVVPOYGGGG NHGGGGNNSG PNSELNTYOY GGGNSALALQ TDARNSDLTI TQHGGGNGAD VGQGSDDSSI DLTQRGFGNS ATLDQWNGKN SEMTVKQFGG GNGAAVDQTA SNSSVNVTQV GFGN-NATAHQ Y* wherein

A Alanine
R Arginine
N Asparagine
D Aspartic acid
C Cysteine
C Cystine
G Glycine
E Glutamic acid
Q Glutamine
H Histidine
I Isoleucine
L Leucine
K Lysine
M Methionine
F Phenylalanine
P Proline
S Serine
T Threonine
W Tryptophan
Y Tyrosine
V Valine
* stop codon The mature curlin protein has a molecular weight of 17 kD when gel-purified, and when determined via the nucleotide sequence it is predicted to contain 122 amino acids providing for a molecular weight of 14,345 daltons.

The invention further comprises a plasmid or phage comprising a nucleotide sequence coding for said fibronectin binding protein.

The invention further comprises a micro-organism comprising at least one hybrid-DNA-molecule according to the above. The micro-organism, *E. coli* HB101/pFnb20 encompassing the plasmid encoding for said nucleotide sequence was deposited May 5, 1988 at Deutsche Sammlung von Mikroorganismen und Zellkulturen, Braunschweig, FRG under the deposition number DSM 4585.

The invention further comprises a method for producing a fibronectin binding protein whereby at least one hybrid-DNA-molecule of the above is introduced into a micro-organism, cultivating said micro-organism in a growth medium, and isolating the protein thus formed and expressed by means of an affinity chromatography on a fibronectin bound to an insolubilized carrier followed by ion exchange chromatography.

A further aspect of the invention comprises a chemical synthesis of the fibronectin binding protein, whereby an amino acid sequence is built up based on said nucleotide sequence encoding for said protein starting from the C-terminal amino acid which is stepwise reacted with the appropriate amino acid, whereby it is finally reacted with the amino acid at the N-terminal end, to form the fibronectin peptide region.

Appropriate carrier proteins can be coupled to the amino acid sequence as well, such as IgG binding regions of protein A.

The invention will be described in the following with reference to the example given below, however, without being restricted thereto.

EXAMPLE

Isolation and characterization of a recombinant clone expressing fibronectin binding.

In a collection of bovine fecal and mastitis isolates of *Eschericia coli*, 58% and 56%, respectively, bound to $^{125}$I-labelled fibronectin. In some of the mastitis isolates the ability to bind to fibronectin was not a stable property. Thus a chromosomal cosmid bank was generated from fecal *E. coli* isolate AO12, since that strain stably expressed binding to fibronectin. Such binding was preferentially expressed when the cells were grown on CFA-agar at temperatures between 26° C. and 32° C. Electron microscopy of 40 fibronectin binding *E. coli* isolates revealed that they all produced coiled surface structures when grown on CFA-agar at 26° C. High magnification of these structures showed them to be thin, wiry fibers with a diameter of about 2 nm. The lateral aggregation of individual fibers produced considerably thicker structures.

Bacteriophage transducing particles carrying portions of the strain AO12 genome cloned into cosmid vector pJB8 were used to transform *E. coli* HB101. Strain AO12 expressed fibronectin binding when grown on CPA plates at 30° C., but to a lesser extent at 37° C. Transductants were thus screened for fibronectin binding after growth on CFA plates for 40 hrs at 30° C. Out of 560 transductants one, AO450, showed fibronectin binding. The recombinant cosmid in this transductant, designated pAO450, was isolated and shown to contain an insert of about 24 kb. pAO450 was digested with restriction endonuclease SalI and subcloned into the vector pACYC184, giving pFnb01. A subclone of pFnb01, viz. pFnb10 containing a 3 kb large SphI-KpnI fragment expressed fibronectin binding when transformed into *E. coli* HB101. The subclone pFnb10 was digested with a series of restriction endonucleases to prepare a restriction map as shown in FIG. 1. To further localize the region on pFnb10 expressing fibronectin binding several subclones were constructed from pFnb10 as were various deletion derivatives. These constructs were tested for their ability to confer binding to *E. coli* HB101. The HpaI and SphI sites delineates the 1.2 kb region required for fibronectin binding as shown in FIG. 1.

The recombinant plasmids shown in FIG. 1 were transformed into the minicell producing strain AA10. Plasmid encoded polypeptides were analysed from $^{35}$S-methionine labelled minicells. Plasmid pFnb10 expressed two polypeptides with molecular masses of 43 kD and 17 kD respectively as shown in FIG. 2. pFnb30 is a deletion derivative of pFnb10 that lacks a 0.9 kb ClaI fragment. This derivative no longer confer fibronectin binding to *E. coli* HB101. The 49 kD polypeptide was still expressed from this clone but the smaller 17 kD polypeptide was missing. The larger polypeptide must be encoded from a gene positioned between the $ClaI_2$ and KpnI sites on pFnb10, since the region between $SphI_1$ and $ClaI_1$ site is to small (0.4 kb) to encompass a gene coding for a 49 kD protein. It is also concluded that the 49 kD polypeptide is not required for fibronectin binding. Plasmids pFnb20 and pFnb58 both expressed fibronectin binding in *E. coli*. The 17 kD polypeptide but not the 49 kD polypeptide was encoded by pFnb20 showing that the gene for the latter polypeptide must span the $SphI_2$ site. The HpaI-$SphI_2$ subclone pFnb56 no longer expressed the 17 kD polypeptide.

Instead a slightly larger polypeptide species of 19 kD was expressed. An 1.5 kb large fragment carrying the aminoglycoside 3 phosphotransferase gene plasmid of pUC-4K was cloned into the single ClaI site of pFnb56 giving pFnb59. This derivative no longer mediated fibronectin binding. In minicells there was no expression of the 19 kD polypeptide. The conclusion is that the 19 kD polypeptide is due to the deletion in the pFnb56 of the normal translational stop codon of the gene for the 17 kD polypeptide giving rise to a slightly longer translational product containing some carboxy terminal amino acids encoded by the vector.

The coiled surface structure could be shared from the surface of HB101/pFnb20 in an omnimixer and such partially purified preparations contained a dominating protein species with a molecular weight of 17 kD. The 17 kD polypeptide was electroeluted onto an Immobulon$^R$ filter and the amino terminal sequence determined by sequential Edman degradation. In order to determine if the isolated protein was the same 17 kD gene product of the structural gene spanning the ClaI, and the HpaI sites in pFnb20 this region was sequenced. One open reading frame consisting of 133 codons was identified spanning the ClaI and HpaI sites. The protein sequence of the 5 amino terminal residues was identical to the DNA sequence specified by codons 2–6 in the open reading frame confirming that the open reading frame identified encodes the subunit protein of the coiled surface structure. The name "curlin" is proposed for this subunit protein, curli for the structure and csgA for the structural gene.

The curlin subunit appears to be strictly different from *E. coli* pilins and *E. coli* pilins have several features in common such such as cleavable signal peptide, two cysteine residues in the amino terminal half, and several conserved amino acids in the amino- and carboxy terminal regions thought to be involved in the subunit—subunit interactions. Likewise no homologoes were found with the N-methyl Phe class of pilus expressed by *Neisseria gonorrhoeae* and many other Gram negative species. Flagellin is not a true secretory protein since it is transported directly from the cytoplasm to the growing tip through the hollow flagellum. The small diameter of the curli suggest that they are assembled from the base. Hence expression of pili is not possible in *E. coli* HB101 when only the major pilus subunit protein is introduced into this strain. In contrast curlin is able to polymerize into curli in the absence of any other cloned gene products.

Furthermore the data implicates that the gene for the 17 kD polypeptide spans the $ClaI_2$ site on pFnb10. Since fibronectin binding was mapped to this gene it was denoted fnbA. *E. coli* pilin proteins are all known to be produced in a precursor form with a cleavable N-terminal signal peptide. To see if the Fnb protein was synthetised from fnbA in a precursor form, minicells expressing Fnb from plasmids were treated with 9% ethanol to prevent processing. There was no appearance of a large molecular weight species suggesting that Fnb is not synthetized with a cleavable signal peptide.

Nucleotide sequence of fnbA gene

Sequence analysis of a $CsCl_2$-purified double-stranded plasmid DNA from pCSG4 was performed by denaturing approximately 4 ug of DNA with 2 M NaOH/2 mM EDTA and neutralizing it with 7.5 M ammonium acetate (pH 5). Appropriate oligonucleotides (1 pmole) were annealed to alkali denatured DNA and sequenced using the Sequenase[R] protocol as described by the manufacturer (United States Biochemical, Cleveland, Ohio). Electrophoresis was performed in a 90 mM TBE buffer system for 2–5 hrs at 45 mA in 8 M urea/6% polyacrylamide gels. Gels were fixed, dried, and exposed to Hyperfilm (Amersham).

```
GGTGTTGTTC CTCAGTACGG CGGCGGCGGT AACCACGGTG
GTGGCGGTAA TAATAGCGGC CCAAATTCTG AGCTGAACAT
TTACCAGTAC GGTGGCGGTA ACTCTGCACT TGCTCTGCAA
ACTGATGCCC GTAACTCTGA CTTGACTATT ACCCAGCATG
GCGGCGGTAA TGGTGCAGAT GTTGGTCAGG GCTCAGATGA
CAGCTCAATC GATCTGACCC AACGTGGCTT CGGTAACAGC
GCTACTCTTG ATCAGTGGAA CGGCAAAAAT TCTGAAATGA
CGGTTAAACA GTTCGGTGGT GGCAACGGTG CTGCAGTTGA
CCAGACTGCA TCTAACTCCT CCGTCAACGT GACTCAGGTT
GGCTTTGGTA ACAACGCGAC CGCTCATCAG TACTAA.
```

This will correspond to the following amino acid sequence

GVVPOYGGG NHGGGGNNSG PNSELNTYOY GGGN-SALALQ TDARNSDLTI TQHGGGNGAD VGQGS-DDSSI DLTQRGFGNS ATLDQWNGKN SEMTVKQFGG GNGAAVDQTA SNSSVNVTQV GFGNNATAHQ Y*

Expression of a curli pili from the original strain AO12 and from HB101 clones expressing the Fnb protein.

*E. coli* strain AO12 grown at 26° C. expressed unusually curli pili like structures when viewed under the electron microscope as shown in FIG. 4. No such structures can be seen on *E. coli* HB101 growing at either 26° C. or 37° C. However, cells of HB101 harboring either pFnb20 of pFnb56 produced large amounts of curli pili structures when grown on CFA medium at 26° C. as shown in FIG. 5. However, no surface structures was found on HB101/pFnb20 and HB101/pFnb56 after growth at 37° C. as shown in FIG. 6, a temperature at which these strains do not express fibronectin binding. No surface structures was found on HB101/pFnb56 deleted for the fnbA gene when grown at either 26° C. or 37° C.

Hence the expression of curli pili in HB101 was strictly correlated to the expression of the Fnb protein. Moreover, the expression of curli pili correlated strictly with the ability of HB101 to bind to fibronectin.

*E. coli* HB101 has been used as a host to clone and express a number of *E. coli* pili types. In no other case has it been possible to obtain surface located pili by only expressing the pilin gene. All other known gene cluster that have been examined today contain additional genes required for transport and assembly of the pilus fiber. When plasmid pFnb20 was present in *E. coli* AA10 curli pili were not observed at 26° C. as shown in FIG. 7 and the cells did not bind fibronectin. Most *E. coli* strains carry in their chromosome, genes for type 1 pili. Both *E. coli* Hb101 and AA10 are unable to form such pili. In the former strain some genes from the type 1 operon are still functioning whereas the entire type 1 gene cluster is deleted in AA10. Plasmid pSJH9 carries all accessory genes required for type 1 pilus formation but is deleted for the fimA gene encoding the major pilin subunit. *E. coli* AA10 harbouring plasmid pSJH9 and pFnb20 did not bind fibronectin. Hence the ability of pFnb20 to express fibronectin binding and curli pili in HB101 does not seem to depend on the complementation from chromosomal type 1 pilus genes. To see if accessory genes located close to fnbA could confer fibronectin binding to *E. coli* AA10 this strain was transformed with the original coamid clone pAO450. Strain AA10/pAO450 was not expressing fibronectin binding. Minicell experiments revealed that strain AA10 is able to synthetize the FnbA protein at 26° C. as well as at 37° C. It is therefore concluded that the FnbA protein can not be expressed for surface localization, nor be assembled into curli pili in this strain.

*Eschericia coli* is a common cause of bovine mastitis. *E. coli* milk isolates from cases of acute mastitis do not differ from the normal fecal *E. coli* flora in the cow. When examining possible virulence associated properties of bovine *E. coli* the ability to bind to fibronectin stands out as a common property shared by 50–80% of the isolates studied. To more closely study fibronectin binding in *E. coli* the fnbA gene was cloned and characterized. The fnb gene codes for a 17,000 dalton protein that is able to polymerize into curli pili like structures when expressed in *E. coli* Hb101.

It is surprising that DNA fragment expressing the FnbA protein, only, could confer piliation in HB101. *E. coli* pili are encoded from an operon consisting of 11 pap genes. The accessory genes papC coding for an 88 kD outer membrane pore protein, and papD expressing a 28 kD periplasmic transport protein are needed in addition to papA, the major subunit gene, to form surface located pili. Even though other classes of pili adhesin gene cluster appear to be less complex and contain fewer genes than the pap system, all carry genes functionally equivalent to papC and papD.

The fact that the fnb plasmid pFnb20 did not confer piliation or curli pili when harboured by *E. coli* AA10 suggests that *E. coli* HB101 express the accessory proteins required for the biogenesis of curli Fnb pili. It is known that *E. coli* HB101 carry some DNA that hybridize to cloned type 1 DNA. However, *E. coli* HB101 do not express type 1 pili if transformed with a type 1 clone deleted for either the fimD (the papC equivalent) or the fimC (the papD equivalent) gene. It is therefore unlikely that it is chromosomal type 1 DNA that encodes the accessory proteins required for the formation of curli Fnb pili. This is further supported by the observation that AA10 cells expressing both the Fnb protein and the accessory of the type 1 did not express fibronectin binding Fnb pili. Strain AA10 is a minicell producing strain. The Fnb protein was clearly synthesized in the minicells although no pili were formed. In the pap system a similar phenotype would have been obtained by mutating the papC gene. Mutations in the papD gene results in a rapid proteolysis of PapA pilin. If similar accessory genes were at hand in the fnb system it could be argued that *E. coli* AA10 lacks a papC equivalent so that the Fnb protein cannot be surface localized.

Curli Fnb pili are formed in HB101 at 26° C. but not at 37° C. In AA10 minicells the Fnb protein is synthesized to the same extent at both temperatures. It is thus suggested that the temperature regulation of piliation and fibronectin binding do not operate at the level of transcription but at the level of pilus biogenesis. Pap pili and many other virulence associated properties are also temperature regulated but the effect of incubation temperature is the reverse of what has been observed concerning the Fnb pili. In the former, system transcription is increased with an increased temperature. This kind of temperature regulation is thought to reflect the adaptation of the micro-organism to the mammalian host.

Wound pathogens such as *Staphylococcus aureus* and *Staphylococcus genera* frequently bind to fibronectin. The temperature of the skin is lower than 37° C. If fibronectin binding of *E. coli* also reflects an adaptation to bind to wounds on the exterior of the host it would be an advantage for the micro-organism to have optimal binding at a temperature lower than 37° C.

Herein there is no evidence given for the fact that fibronectin binding curli pili actually plays a role in the pathogenesis of bovine mastitis. The frequent presence of ulcers, due for example to machine milking on the udder might, however, enable colonization of fibronectin binding *E. coli*. Fibronectin is a large glycoprotein known to bind to a large set of proteins. It is therefore uncertain how specific the interaction is between fibronectin and Fnb pili. The fnbA cosmid pAO450 was the single one out of 560 cosmids tested that expressed fibronectin binding in HB101. It is thus believed that this gene is the sole determinant of fibronectin binding in *E. coli* AO12.

Materials and methods.

Bacterial strains and growth conditions.

Except for the bovine isolate AO12 all bacterial strains are derivatives of *E. coli* K-12, HB101, ( $hsdr^-$, $hsdm^-$, recA13, supE44, lacZ4, leuB6, proA2, thr-1, $Sm^r$) were used as host in the fibronectin binding assay. JM83 (ara, (lac-proAB), rpsL, 80, lacZ M15) were used as host in all transformation experiments. For protein expression analyses a recA derivative of P678-54 (Lund et al, J. Bact. 162, 1293–1301), AA10 (obtained from P. Orndorf, Stanford University, Stanford, Calif.) was used. M13 cloning and phage propagation were carried out in strain JM103 (Messing et al. N.A.R. 9:309–321). Strain AO12 is a bovine fecal isolate obtained from a healthy cow.

Other *E. coli* K12 strains were tested and analyzed for the production of curli and the ability to bind fibronectin. Strain C600 (thr-1 leuB6 lacY1 suoE44 rfbD1 thi-1 tonA21) was found to bind fibronectin when grown on CFA-agar at 26° C., at which temperature it also produced curli. The proA2 deletion mutant AB1157 did not, as expected express neither property. The minicell producing *E. coli* K12 strain AA10 carries the crl region as revealed by DNA—DNA hybridization using the 1.5 kb large BglII-SphI fragment as a probe, but did not express curli and did not bind soluble fibronectin.

Bacteria were normally grown in L-broth (Bertani 1951). For the fibronectin binding assay bacteria were grown on CFA-agar (Inf. Imm, 25, 738–748, Evans) and containing 0.005% magnesium sulphate and 0.0005% magnesium chloride in 2% Bacto agar (Difco). Competent cells for transformation were prepared with 50 mM $CaCl_2$ (Gene 6, 23–28, Dagert).

The antibiotics ampicillin (100 ug/ml), kanamycin (50 ug/ml) and chloramphenicol (20 ug/ml) were used for selection of plasmid-containing strains. Unless otherwise stated incubation of bacterial cultures was carried out at 37° C.

The present fibronectin binding protein will sometimes be synthesized in the cell wall and is not expressed as a pili. This protein thus synthesized can be isolated as well by known bio-chemical methods, such as affinity chromatography.

Recombinant DNA technique.

Restriction endonucleases, T4 ligase and Sequence™ were used according to the conditions recommended by the manufacturer (New England, Biolabs, PL, Pharmacia, Uppsala, Sweden; USB, Cleaveland, Ohio, USA).

Isolation of plasmid DNA, agarose gel electrophoresis, transformation of *E. coli* and isolation of DNA fragments from polyacrylamide gels were performed essentially as described by Maniatis et al (1982). Relevant fragments were subcloned into M13mp18 and M13mp19 vector (Messing, J and Vieira, J, Gene, 19, 269–272 (1982)), and sequenced using the dideoxy chain terminating method of Sanger et al, PNAS, 74, 5463–5467. For DNA sequencing the bacteriophage T7 DNA polymerase, and Sequenase™ were used. The primer used was Universal M13 17mer and synthesized 20mer oligonucleotides supplied by Symbicom, Umeå, Sweden.

Isolation of chromosomal and plasmid DNA.

DNA was isolated as described by Lund et al. Plasmid DNA from clones carrying recombinant DNA was isolated by the alkaline lysis procedure (Maniatis, CSH, N.Y., USA).

Cosmid cloning procedure.

Chromosomal DNA purified from *E. coli* AO12 were partially cleaved with endonuclease Sau3AI. The DNA was size fractionated on a 10–40% linear sucrose gradient. Fractions containing DNA fragments larger than 20 kb in size were pooled and ligated into the BamHI site of the cosmid vector pJB8 as described by Maniatis, CSH Lab, N.Y. USA. Recombinant molecules were packaged in vitro into particles using a lambda DNA in vitro packaging kit (code N.334, Amersham). The phage was then used to infect *E. coli* HB101 by selecting for ampicillin resistant clones after growth on CFA agar plates at 30° C. for 40–48 hrs.

Plasmid construction

The cosmid clone pAO450 carried a roughly 24 kb large chromosomal insert. Plasmid pFnb01 was constructed by subcloning a 4.9 kb large SalI fragment from this cosmid into pACYC184. An internal 3 kb large $SphI_1$-KpnI from pFnb01 was cloned into pUC18 (Messing) giving pFnb10. A number of subclones from pFnb10 were generated by cloning into the polylinker site in pUC18. Plasmid pFnb59 is a ClaI cut back derivative of pFnb10. Subclones were constructed as follows. pFnb10 consists of the 3.0 kb KpnI-PstI fragment of the original clone ligated into the polylinker cloning cassette of pUC18, while pFnb30 is a ClaI deletion derivative of pFnb10. Plasmid pFnb20 was obtained by cloning the 1.5 kb SphI-BglII fragment from the original plasmid into pUC18. Analysis of this construct which lacks the 5' terminal end of the gene coding for the 49 kD peptide showed that this protein was not necessary for curli production or for fibronectin binding. Plasmids pFnb56 and pFnb46 are SphIHpaI and ClaI-BglII subclones, respectively of pFnb10 in pUC18. Plasmid pFnb59 was obtained by first subcloning the KpnI-BglII fragment of the original plasmid in pUC18 and then inserting the aminoglycoside-3'-phosphotransferase gene (APH) from the mobilization plasmid pUC-4K into the $ClaI_1$ site. To perform the fibronectin binding assay bacteria were grown on CFA-agar plates for 42–48 hrs at 26° C. or 37° C.

AccI digested plasmid pUC-4K (Pharmacia, Uppsala, Sweden) carrying the kanamycin resistance gene from transposon Tn903 coding for aminoglycoside 3 phosphotransferase (APH) was ligated to ClaI digested pFnb56. Transformants in HB101 were screened for ampicillin and kanamycin resistance. One such clone carrying the $Kana^R$ fragment at the ClaI site was denoted pFnb59.

Fibronectin binding assay.

The fibronectin binding assay was a modification of the procedure described by G. Fröman et al, (JBC, 259, 14899–14905). Bacteria were inoculated on CFA plates for 42–48 hrs at 26° C. or 37° C. Cells were resuspended in cold phosphate-buffered saline (pH 7.5) to an optimal density of $10^9$ cfu/ml. 100 ul of cells were added to an assay tube containing 1 ml of PBS+0.1% Tween 80+100 ul of $^{125}$I-fibronectin ($5\times10^5$ cpm) and the mixture was end over incubated in room temperature for 1 hr. Tubes were centrifuged in Eppendorf centrifuge for five min. Supernatants were carefully aspirated. The radioactivity in the pellet was measured in a liquid scintillation counter (LKB-Wallac).

Analysis of protein expression in minicells.

Plasmid constructs were transformed into the minicell-producing strain AA10. Preparation and labelling of minicells with $^{35}$S-methionine were as described by Thompson and Achtman (Mol. Gen. Genet. 165, 295–304 (1978)).

The radioactive samples were separated on linear 15% (wt/vol) SDS-polyacrylamide gels (Laemmli, UK, Nature, 227, 880–885, (1970)). The gels were fixed, stained, destained, and exposed to X-ray film (DuPont) for 1–5 days. Molecular weight standards were from Pharmacia Fine Chemicals, Uppsala, Sweden.

Precursor form of proteins encoded by different constructions were monitored after radiolabelling of minicells in the presence of 9% ethanol (Palva, J. Bact., 146, 325–330) and analysed on SDS-polyacrylamide gels.

Electron microscopy.

Electron microscopy was performed using a JEOL 100B microscope with 100-mesh copper grids coated with thin films of 2% Formvar. Bacteria from CFA agar plates were resuspended in 10 mM Tris-HCl, -pH 7.5+10 mM $MgCl_2$, and placed on the grid. Grids were washed with buffer and negatively stained for 5 sec. with 3.55& ammonium molybdate, followed by washing with redistilled water. The present fibronectin binding protein can be used for immunization, whereby the protein, preferably in combination with a fusion protein to create a large antigen to respond to, or the pili shaken off from the *E. coli* expressing the curli pili when grown around about 30° C., preferably at 26° C., or the inactivated *E. coli* comprising the curli pili consisting of the fibronectin binding 17 kD protein, is injected in dosages causing immunological reaction in the host mammal. Thus the fibronectin binding protein can be used in vaccination of ruminants against mastitis caused by *E. coli* infections. The fibronectin binding protein can further be used for immunization against urinary tract infections, normally caused by *E. coli*, or intestinal infections normally caused by *E. coli*, such as ulcerous colitis. The fibronectin binding protein of this invention has been shown to form antibodies against *E. coli* related infections.

Further, the fibronectin binding protein can be used to block an infection in an open skin wound by wound treatment using the fibronectin binding protein in a suspension. Thus the fibronectin binding protein can be used for the treatment of wounds, e.g., for blocking protein receptors, or for immunization (vaccination). In the latter case the host body produces specific antibodies which can protect against invasion of bacterial trains comprising such a fibronectin binding protein. Hereby the antibodies block the adherence of the bacterial strains to damaged tissue.

Examples of colonizing of tissue damage are:

a) colonizing of wounds in skin and connective tissue, which wounds have been caused by a mechanical trauma, chemical damage, and/or thermical damage;

b) colonizing of wounds on mucous membranes such as in the mouth cavity, or in the mammary glands, urethra, or vagina;

c) colonizing on connective tissue proteins, which have been exposed by minimal tissue damage (micro lesion) in connection with epithelium and endothelium (mastitis, heart valve infection, hip exchange surgery).

When using the present fibronectin binding protein or a synthesized amino acid polypeptide for the purpose of immunization (vaccination) in mammals, including humans, the protein, or polypeptide, or curli pili, or whole inactivated bacteria is dispersed in sterile, isotonic saline solution, optionally while adding a pharmaceutically acceptable dispersing agent. Different types of adjuvants can further be used in order to sustain the release in the tissue, and thus expose the protein for a longer time to the immuno defence system of a body. The injectible solutions will usually be given subcutaneously or intramuscularly.

A suitable dosage to obtain immunization is 0.5 to 5 ug of fnb protein per kg body weight and injection by immunization. In order to obtain durable immunization, vaccinations should be carried out at more than one consecutive occasions with an interval of 1 to 3 weeks, preferably at three occasions.

When using the present fnb protein for topical local administration the protein is dispersed in an isotonic saline solution to a concentration of 25 to 250 u per ml. The wounds are then treated with such an amount only to obtain a complete wetting of the wound surface. For an average wound thus only a couple of milliliters of solution are used in this way. After treatment using the protein solution the wounds are suitably washed with isotonic saline or another Suitable wound treatment solution.

Further the fibronectin binding protein, or the synthesized polypeptide of the present invention can be used to diagnose bacterial infections caused by *E. coli* strains, whereby a fibronectin binding protein of the present invention is immobilized on a solid carrier, such as small latex or $Sepharose^R$ beads, whereupon sera containing antibodies are allowed to pass and react with the fibronectin binding protein thus immobilized. The agglutination is then measured by known methods.

Further the fibronectin binding protein or the polypeptide can be used in ELISA test (Enzyme Linked Immuno Sorbent Assay; E Engvall, Med. Biol. 55, 193, (1977)). Hereby wells in a polystyrene microtitre plate are coated with the fibronectin binding protein and incubated over night at 4° C. The plates are then thoroughly washed using PBS containing 0.05% Tween 20, and dried. Serial dilution of the patient serum is made in PBS-Tween, are added to the wells, and incubated at 30° C. for 1.5 hrs. After rinsing antihuman-IgG conjugated with an enzyme, or a horseradish peroxidase, or an alkaline phosphatase is added to the wells and incubated at 30° C. for 1.5 hrs, whereupon when the IgG has been bound thereto, and after rinsing, an enzyme substrate is added, a p-nitrophosphate in case of an alkaline phosphatase, or orthophenylene diamine substrate (OPD) in case a peroxidase has been used, respectively. The plates comprising the wells are thus then rinsed using a citrate buffer containing 0.055% OPD, and 0.005% $H_2O_2$, and incubated at 30° C. for 10 min. Enzyme reaction is stopped by adding a 4N solution of $H_2SO_4$ to each well. The color development is measured using a spectrophotometer.

Depending on the type of enzyme substrate used a fluoroscense measurement can be used as well.

Another method to diagnose *E. coli* infections is by using the DNA gene probe method based on the fnb protein sequence or the synthetic polypeptide sequence. Thereby the natural or synthetic DNA sequences are attached to a solid carrier, such as a polystyrene plate as mentioned above, by e.g., adding a milk in the case of diagnosing a mastitis, to the surface. The DNA gene probe, optionally labelled enzymatically, or by a radioactive isotope is then added to the solid surface plate comprising the DNA sequence, whereby the DNA gene probe attaches to the sequence where appearing. The enzyme or the radioactive isotope can then readily be determined by known methods.

Above the term fibronectin binding protein includes any of the polypeptide sequences as well, which polypeptide sequences form the minimal fibronectin binding site of the complete protein.

We claim:

1. An isolated, purified DNA sequence comprising a nucleotide sequence from *E. coli* coding for a protein or polypeptide having fibronectin binding ability with the following amino acid sequence:

GVVPQYGGGG NHGGGGNNSG PNSELNTYQY
GGGNSALALQ TDARNSDLTI
TQHGGGNGAD VGQGSDDSSI DLTQRGFGNS
ATLDQWNGKN SEMTVKQFGG
GNGAAVDQTA SNSSVNVTOV GFGNNATAHO Y*.

2. An isolated, purified DNA sequence according to claim 1, characterized in that it comprises the following nucleotide sequence GGTGTTGTTC CTCAGTACGG CGGCGGCGGT
AACCACGGTG GTGGCGGTAA
TAATAGCGGC CCAAATTCTG AGCTGAACAT
TTACCAGTAC GGTGGCGGTA
ACTCTGCACT TGCTCTGCAA ACTGATGCCC
GTAACTCTGA CTTGACTATT
ACCCAGCATG GCGGCGGTAA TGGTGCAGAT
GTTGGTCAGG GCTCAGATGA
CAGCTCAATC GATCTGACCC AACGTGGCTT
CGGTAACAGC GCTACTCTTG
ATCAGTGGAA CGGCAAAAAT TCTGAAATGA
CGGTTAAACA GTTCGGTGGT
GGCAACGGTG CTGCAGTTGA CCAGACTGCA
TCTAACTCCT CCGTCAACGT
GACTCAGGTT GGCTTTGGTA ACAACGCGAC
CGCTCATCAG TACTAA.

3. A plasmid or phage comprising the nucleotide sequence according to claim 2.

4. Micro-organism containing at least a plasmid or a phage according to claim 3.

5. A method for producing a fibronectin binding protein or polypeptide, said method comprising a) introducing a purified DNA sequence according to claim 2 into a micro-organism;

b) cultivating said micro-organism in a colonization factor antigen growth medium at a temperature of 25–30° C. for 35–50 hrs; and c) isolating the protein thus expressed and formed as a curli pili.

6. A micro-organism transformed by the DNA of claim 2.

7. A method for producing a fibronectin binding protein or polypeptide, said method comprising a) introducing a purified DNA sequence according to claim 1 into a micro-organism;

b) cultivating said micro-organism in a colonization factor antigen growth medium at a temperature of 25–30° C. for 35–50 hrs; and c) isolating the protein thus expressed and formed as a curli pili.

8. A micro-organism transformed by the DNA of claim 1.

9. A plasmid or phage comprising a nucleotide sequence from *E. coli* coding for a protein or a polypeptide having fibronectin binding ability with the following amino acid sequence:

GVVPQYGGGG NHGGGGNNSG PNSELNTYQY
GGGNSALALQ TDARNSDLTI
TQHGGGNGAD VGQGSDDSSI DLTQRGFGNS
ATLDQWNGKN SEMTVKQFGG
GNGAAVDQTA SNSSVNVTOV GFGNNATAHO Y*.

10. A micro-organism transformed by the plasmid or phage of claim 9.

11. A plasmid pFnb20 as contained in the *E. coli* HB101 strain having the deposit number DSM 4585.

12. A micro-organism transformed by the plasmid of claim 11.

13. The *E. coli* strain having the deposit number DSM 4585.

14. An isolated *E. coli* strain expressing a mature curlin protein, said protein having fibronectin binding activity, wherein said *E. coli* did not express mature curlin protein prior to transformation with a DNA molecule encoding said protein, wherein said DNA molecule has the nucleotide sequence GGTGTTGTTC CTCAGTACGG CGGCGGCGGT
AACCACGGTG GTGGCGGTAA
TAATAGCGGC CCAAATTCTG AGCTGAACAT
TTACCAGTAC GGTGGCGGTA
ACTCTGCACT TGCTCTGCAA ACTGATGCCC
GTAACTCTGA CTTGACTATT
ACCCAGCATG GCGGCGGTAA TGGTGCAGAT
GTTGGTCAGG GCTCAGATGA -continued CAGCTCAATC GATCTGACCC AACGTGGCTT CGGTAACAGC GCTACTCTTG ATCAGTGGAA CGGCAAAAAT TCTGAAATGA CGGTTAAACA GTTCGGTGGT GGCAACGGTG CTGCAGTTGA CCAGACTGCA TCTAACTCCT CCGTCAACGT GACTCAGGTT GGCTTTGGTA ACAACGCGAC CGCTCATCAG TACTAA.

15. An *E. coli* strain according to claim 14, wherein said strain is obtained by transforming *E. coli* with a DNA molecule encoding said mature curlin protein.

16. An isolated *E. coli* strain expressing a mature curlin protein, said protein having fibronectin binding activity, wherein said *E. coli* did not express mature curlin protein prior to transformation with a DNA molecule encoding said protein, wherein said mature curlin protein has the amino acid sequence GVVPQYGGGG NHGGGGNNSG PNSELNTYQY GGGNSALALQ TDARNSDLTI TQHGGGNGAD VGQGSDDSSI DLTQRGFGNS ATLDQWNGKN SEMTVKQFGG GNGAAVDQTA SNSSVNVTOV GFGNNATAHQ Y*.

17. An *E. coli* strain according to claim 16, wherein said strain is obtained by transforming *E. coli* with a DNA molecule encoding said mature curlin protein.

* * * * *